United States Patent [19]

Bonhard et al.

[11] 4,136,093
[45] Jan. 23, 1979

[54] HEMOGLOBIN PREPARATION WITH INCREASED OXYGEN RELEASE

[75] Inventors: Klaus Bonhard, Hanau; Uwe Boysen; Hans Schleubner, both of Frankfurt am Main, Germany

[73] Assignee: Biotest-Serum-Institut GmbH, Frankfurt am Main, Germany

[21] Appl. No.: 789,759

[22] Filed: Apr. 21, 1977

[30] Foreign Application Priority Data

Apr. 23, 1976 [DE] Fed. Rep. of Germany ....... 2617822
Mar. 31, 1977 [DE] Fed. Rep. of Germany ....... 2617882

[51] Int. Cl.$^2$ ........................................... C07C 103/52
[52] U.S. Cl. ........................... 260/112.5 R; 260/112 B
[58] Field of Search ...................... 260/112.5 R, 112 B

[56] References Cited

U.S. PATENT DOCUMENTS 4,001,200  1/1977  Bonsen et al. ................ 260/112.5 R

OTHER PUBLICATIONS

Benesch, et al., Biochemistry 11, 1972, pp. 3576–3582.
Benesch, et al., Biochem. and Biophys. Res. Commun. 63, 1975, pp. 1123–1129.

Primary Examiner—Delbert R. Phillips
Attorney, Agent, or Firm—Sprung, Felfe, Horn, Lynch & Kramer

[57] ABSTRACT

Hemoglobin preparation suited for intravenous injection with increased oxygen release in relation to erythrocytes or hemoglobin solution, comprising a substantially pyrogen-free condensation product of hemoglobin and pyridoxal phosphate having a retention time in the blood vessel from about 2 to 9 hours. It is produced by washing human erythrocytes at least four times with a weakly alkaline solution, then hemolyzing and treating the material with a cation exchange resin in the H+ form until the pH value has dropped to about 5 to 5.5, separating the material from resin and any precipitated stroma, diluting the material to a hemoglobin concentration of about 5 to 9%, adjusting the pH to about 7 to 9, displacing any oxygen therein, and adding about 0.25 to 1.25 g of pyridoxal-5-phosphate per liter of hemoglobin solution of 5 to 9% concentration. To increase the retention time still further there can be included the further steps of treating the solution with a borohydride and then with a dialdehyde thereby to cross-link the hemoglobin molecules in said erythrocytes, and separating uncross-linked hemoglobin from the residual solution of the desired cross-linked hemoglobin.

13 Claims, 6 Drawing Figures

HEMOGLOBIN PREPARATION WITH INCREASED OXYGEN RELEASE

The invention relates to a hemoglobin preparation suited for intravenous injection with increased oxygen release in relation to erythrocytes or hemoglobin solutions.

The oxygen half-saturation pressure of hemoglobin (Hb), called the $P_{50}$ value, is known to be 27 mm Hg in the intact erythrocyte. That measure of the readiness to give up oxygen is determined, apart from the intraerythrocytic pH value of 7.25, primarily by the 2,3-diphosphoglycerate (DPG) content. In the case of all infusion preparations based on freely dissolved hemoglobin or derivatives thereof, the pH value of the blood plasma, about 7.4, is the determining factor since they must necessarily transport the oxygen under these conditions. This fact alone results in a leftward displacement of the oxygen-binding curve corresponding to a reduction of the $P_{50}$ value to about 24 mm Hg at best. Now when such a hemoglobin solution has been infused, 2,3-diphosphoglycerate unbound in the dissociation equilibrium is immediately secreted through the kidneys because of its small molecular size. The DPG is bound to the Hb in saltlike manner and then dissociates at a corresponding rapid rate so that in a short time all of the Hb freely dissolved in the blood vessel is stripped. As a result, the $P_{50}$ value drops to between 15 and 17 mm Hg. A higher $P_{50}$ value is indicative of an increased readiness of a preparation to give up oxygen.

The background of the invention and its departure from the art will be further described hereinbelow with reference to the accompanying drawing, wherein.

Figure 1:
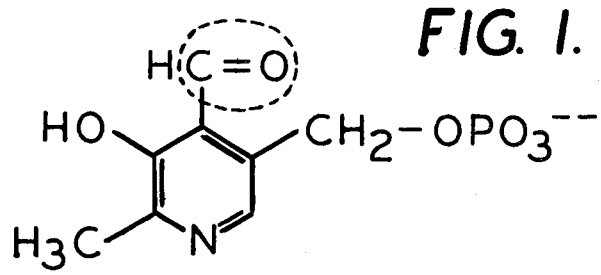
FIG. 1 is the structural formula of the pyridoxal-5-phosphate anion.

Up to now no hemoglobin preparation has been found that will readily give up oxygen for supplying the tissue with oxygen. It is known that pyridoxal-5-phosphate (FIG. 1) is preferentially bound also at the same point of the Hb molecules as DPG, but surprisingly it is bound to the hemoglobin very much more firmly than diphosphoglycerate. The model preparation of hemoglobin and pyridoxal phosphate described by R. E. Benesch, R. Benesch, A. Benk, R. Renthal and B. A. Bray in Proc. I. Interamer. Symp. Haemoglobins, Caracas (1969), "Genetical, functional and physical studies of hemoglobins," pp. 134–142 (Karger, Basel 1971) cannot be used as an infusion solution as it gives rise to pyrogenic reactions.

Surprisingly, it has now been found that it is possible to produce a hemoglobin preparation suited for intravenous injection with increased oxygen release in relation to erythrocytes which is formed by a condensation product of hemoglobin and pyridoxal phosphate and produces no pyrogenic reaction. Because of its favorable affinity for oxygen, such a preparation can be used intravenously therapeutically. In this condensation product there is present a hemoglobin tetramer with a statistical distribution of pyridoxal phosphate over the hemoglobin. The preparation itself has a $P_{50}$ value of 32 mm Hg with a pH value of 7.4. The retention time of such a preparation in the blood vessel is about two hours.

Such nonpyrogenic infusion solutions (Hb/PP) which act in the circulating blood as highly effective oxygen donors can be prepared by departing from the process for producing hemoglobin of R. E. Benesch and R. Benesch (Proc. of the National Academy of Science USA 59, pp. 526–532 (1968), and proceeding as follows:

Human erythrocytes are treated at about 10 to 15° C. for about 5 to 15 minutes with diluted solutions of $\beta$-propiolactone, the proportion of $\beta$-propiolactone (BPL) ranging from about 4 to 12 grams per liter of erythrocyte sediment, then washed free of excess BPL and its reaction products with a weakly alkaline solution and hemolyzed by stirring in about 1 to 2 liters of aqua pro injections per liter of erythrocyte sediment. However, this preliminary treatment is not absolutely necessary for production of the desired preparation. Simple repeated washing will suffice. The hemolysate obtained is then treated with a cation exchanger in the H+ form until the pH value has dropped to about 5.0 to 5.5, and at a pH of about 5.5 to 5.7, possible after adjustment with about 1N caustic soda solution, is rid of the resin and the precipitated stroma mass by cold centrifugation. By dilution with aqua pro injectione, the hemoglobin concentration is adjusted to about 5 to 9%, and the pH value to about 7 to 9 with about 1N caustic soda solution. The electrolytes are made up to concentrations corresponding to blood plasma by appropriate salt additions. About 22 g of glucose monohydrate is added per liter, the solution is once more clarified by cold centrifugation, if indicated, and then agitated in a closed vessel for about 10 minutes under an absolute pressure of 20 mm Hg, the reaction mass is placed under a pure nitrogen gas atmosphere and flushed for about 30 to 60 seconds, mixed with about 0.25 to 1.25 g of pyridoxal-5-phosphate monohydrate per liter of about 5 to 9% hemoglobin solution, agitation under the nitrogen atmosphere then being continued for about 1 hour at room temperature. About 1N caustic soda solution is then added dropwise until a pH value of about 7.6 at about 20° C. is obtained. Finally, the solution is sterile-filtered in infusion units of about 300 ml of 500 ml.

Figure 2:
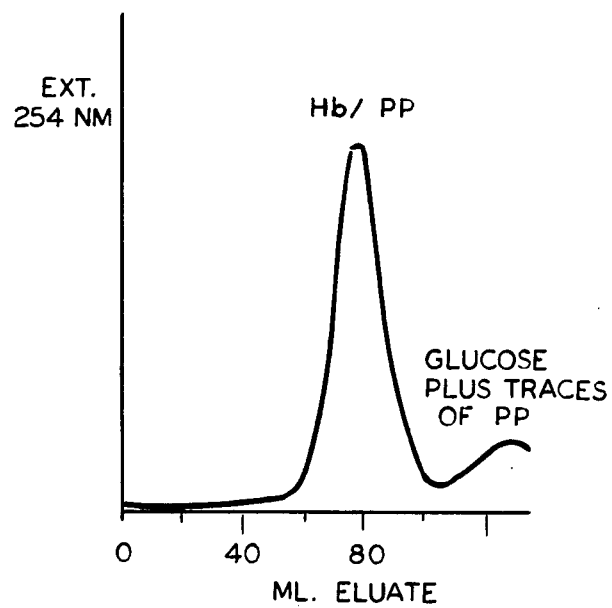
FIG. 2 is an ir extinction curve at 254 nm of the eluate of a Sephadex G chromatogram of a product in accordance with the prior art.

The columnar chromatogram of such preparations (Sephadex G-150, 90×1.5 cm, 0.3 ml volume deposited) is shown in FIG. 2 of the accompanying drawings.

The $P_{50}$ values of the preparation in accordance with the invention at a pH value of 7.45 range from about 30 to 40 mm Hg and thus are considerably greater than the $P_{50}$ value of the hemoglobin in the erythrocyte.

It has been found, moreover, that through further modification of such molecules, which by reason of the binding of pyridoxal phosphate to the hemoglobin are capable of improved oxygen delivery to the tissue and whose retention time in the blood is about two hours, the length of time for which they are fully effective in the circulating blood can be at least doubled while their therapeutic function is maintained. This is accomplished by the following procedure:

Human erythrocytes are treated repeatedly, and specifically at least four times, with weakly alkaline wash solutions, then hemolyzed and treated with a cation exchanger in the H+ form until the pH value has dropped to between about 5.0 and 5.5, then rid of resin and precipitated stroma mass by cold centrifugation, diluted with water to a desired hemoglobin concentration of between about 5 and 9%, then adjusted to a pH value of about 7 to 9 with about 1N caustic soda solution, agitated for about 10 minutes under an absolute pressure of about 20 mm Hg, then agitated with the introduction of nitrogen until the oxygen in the vessel has been displaced with pure nitrogen, after which about 0.25 to 1.25 g of pyridoxal-5- phosphate per liter of about 5 to 9% hemoglobin solution is added and agitation is continued for 1 hour under nitrogen at room temperature, whereupon it is mixed by stirring for another 20 minutes at room temperature with about 5 to 10 times the molar quantity of sodium borohydride in relation to the pyridoxal phosphate, followed by another evacuation, whereupon a dialdehyde is added to the hemoglobin in about 9 times the molar quantity, followed by about 45 minutes' agitation under nitrogen, uncrosslinked hemoglobin then being separated by salting out or ultrafiltration, the concentrated crosslinked preparation then being adjusted with about 1N caustic soda solution to a pH value of about 7.6 at 20° C., made up to concentrations corresponding to blood plasma with appropriate salt additions, about 22 g of glucose monohydrate then being added per liter, followed by sterile filtration.

The uncrosslinked hemoglobin may be diminished by either of the following methods:

1. An about 4M ammonium sulfate solution in a volume about 0.8 to 1.0 times that of the hemoglobin preparation is gradually stirred in to salt out the crosslinked hemoglobin. The precipitate centrifuged off is dissolved in water and dialyzed against an about 0.5% common salt solution for elimination of the ammonium sulfate and all excess auxiliary chemicals. The last traces are removed with a mixed-bed exchanger.
2. The hemoglobin preparation is passed through an H1P 100 hollow-fiber cartridge (manufactured by Amicon Corporation, 21 Hostwell Avenue, Lexington, Mass.). Uncrosslinked hemoglobin is preferentially separated by pressure through ultrafiltration and thereby diminished in the unfiltrate.

In this process, the pyridoxal phosphate is first allowed to act upon the hemoglobin, and the azomethine (Schiff base) linkages are then reduced to secondary amino bonds with nascent hydrogen from sodium borohydride.

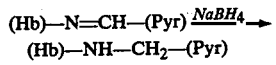
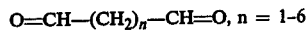

A dialdehyde of the general formula $O=CH-(CH_2)_n-CH=O, n = 1-6$ is then allowed to act upon the molecules. This produces an aggregation of the modified hemoglobin molecules to larger structures.

In accordance with the invention, dialdehydes, and particularly those having straight carbon chains with from three to eight carbon atoms, such as malonic dialdehyde, succinic dialdehyde, glutaric dialdehyde, adipic dialdehyde, and suberic aldehyde conforming to the general formula $OCH-(CH)_n-CHO$, where n represents a value from 1 to 6, are suited for the treatment.

Figure 3:
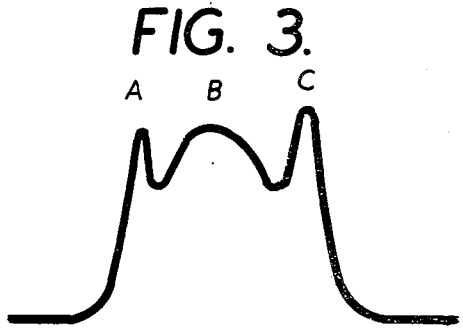
FIG. 3 is a similar generalized curve of a product in accordance with the present invention.

The product of this process, $(Hb/PP)m$, in accordance with FIG. 3 of the accompanying drawing is formed of —

A = highly crosslinked pyridoxalated hemoglobin (m>3)
B = oligomer-crosslinked pyridoxalated hemoglobin (m = 2–3)
C = uncrosslinked pyridoxalated hemoglobin (m = 1)

Even expired blood-bank erythrocytes may be used as starting material for both process modifications.

Apart from a satisfactory pyrogen test, the infusion preparation composed of Hb/PP in accordance with the invention was tested on rats and mice for acute toxicity. As much as 50 ml of an 8% solution per kilogram of body weight was tolerated by the rats intravenously without abnormal behavior and without conspicuous symptoms. Since mice survived an intravenous dose of 100 ml per kilogram of body weight, it was determined, in accordance with Thaer: "Grundlagen der experimentellen Arzneiforschung" (Fundamentals of Experimental Drug Research) (1965) that the $LD_{50}$ is greater than 50 ml/kg of body weight and that the substance may be classed as "relatively harmless."

In contradistinction to the product of R. E. and R. Benesch, it was possible to demonstrate in the case of the preparation in accordance with the invention, on the basis of a constant $P_{50}$ value, that the Schiff base linkages of the pyridoxal phosphate to the amino group of the N-terminal valine of the β chain of the hemoglobin is resistant to dialysis treatment in vitro. An exhaustive dialysis against 0.9% common salt solution was carried out at 10° C.

| Result Preparation | $P_{50}$ (mm Hg) Before dialysis | After dialysis |
|---|---|---|
| Hb/PP 731017 | 32 | 33 |
| Hb/PP 731013 | 39 | 37 |

See also literature citation R. E. Benesch et al. 1971.

The superior effectiveness of the Hb/PP preparation under the physiological conditions of circulating blood is manifest also in animal experiments. Even under a normal venous oxygen partial pressure of 40 mm Hg the preparation releases amounts of oxygen to the tissue which the freely dissolved normal hemoglobin attains only under pathological conditions, that is to say, when the venous $PO_2$ has dropped to about 20 mm Hg. (K. Messmer et al., in preparation.)

The preparations in accordance with the invention and their manufacture will now be explained further in terms of the examples which follow.

EXAMPLE 1

The erythrocyte sediment of a blood preserve (about 270 ml) stored for 4 weeks is mixed by stirring for 10 minutes with one-third of its volume of a 1.6% common salt solution containing 1.2% β-propiolactone. The erythrocytes are centrifuged off at 0° C. and, after drawing off of the supernatant matter and the thrombocyte skin, washed four times with from one to two times the volume of the following solutions on the cooling centrifuge:

1. 3.8% sodium bicarbonate/water
2. 3.8% sodium bicarbonate/water
3. 1:1 mixture of 1.6% common salt/3.8% bicarbonate solution
4. 1.6% common salt solution For hemolysis, the washed erythrocytes are stirred into an amount of aqua pro injectione which corresponds to the initial erythrocyte volume and mixed with a cation-exchanger suspension in the $H^+$ form — for example, DOWEX 50 WX 8 — until the pH value drops to 5. This is followed by neutralization to a pH value between 5.5 and 5.7 with 1N caustic soda solution and separation of stroma and resin by cold centrifugation and decanting. The supernatant matter is diluted with aqua pro injectione to 8.6% hemoglobin, adjusted to a pH of 7.5 with 1N caustic soda solution and mixed with 3.6 g of sodium chloride, 22 g of glucose monohydrate, 0.29 g of potassium chloride, 0.23 g of calcium chloride dihydrate, and 0.25 g of magnesium sulfate heptahydrate per liter of solution.

This is followed by further cold centrifugation, decanting and agitation in a closed vessel for 10 minutes under an absolute pressure of 20 mm Hg.

The last remaining oxygen is expelled by injection of pure nitrogen so that the hemoglobin then is present primarily in the desoxy form. This is reacted with 1.1 g of pyridoxal-5-phosphate monohydrate per liter of solution (corresponding to about 3.5 moles of pyridoxal phosphate per mole of Hb tetramer) by agitation for 1 hour at 20° C. under nitrogen after prior addition of 2.12 g of sodium bicarbonate per liter.

This is followed by a final adjustment to a pH value of 7.6 at 20° C. with 1N caustic soda solution and sterile filtration.

Yield: About 400 ml of solution containing 8% Hb. $P_{50}$ value at pH 7.45: 32 mm Hg.

EXAMPLE 2

The combined erythrocyte sediments of six fresh blood preserves (about 1.5 l) are treated in accordance with Example 1, but for 5 minutes with 2.0% β-propiolactone/1.6% sodium chloride solution. Hemolysis is effected with double the volume of erythrocytes of about 3 liters aqua pro injectione.

Before the addition of 0.82 g of pyridoxal phosphate monohydrate per liter of solution — consistent with the dilution — the pH value is adjusted to 9.0, in contrast to Example 1, with 1N caustic soda solution, and agitation under nitrogen is carried on for 2 hours.

After analogous further treatment, there are obtained: 4 liters of an Hb/PP solution containing 6% of Hb. $P_{50}$ value: 32 mm Hg.

EXAMPLE 3

The erythrocyte sediment of a blood preserve 10 days old is made to undergo four washing operations as in Example 1 but without prior β-propiolactone treatment. However, the washed erythrocytes are hemolyzed in 450 ml of aqua pro injectione (stronger dilution). For the reaction with 1.1 g of pyridoxal-5-phosphate monohydrate per liter of solution (corresponding to 5 moles of pyridoxal phosphate per mole of Hb tetramer), however, the pH value is adjusted to 7.3. followed by agitation for 2 hours under nitrogen at room temperature.

After the usual final electrolyte adjustment, about 700 ml of Hb/PP solution containing 5.5% Hb is obtained. $P_{50}$ value: 39 mm Hg.

EXAMPLE 4

Combined erythrocyte sediments of 25 expired blood preserves (about 6 l) are agitated in accordance with Example 1, but only for 5 minutes with the β-propiolactone/common salt solution indicated. By contrast to Example 1, the pH value is adjusted to 7.0 prior to the addition of the pyridoxal phosphate.

At the completion of the further treatment carried out in accordance with Example 1, 10.5 liters of an Hb/PP preparation containing 8% Hb and having a $P_{50}$ value of 34 mm Hg is obtained.

EXAMPLE 5

100 ml of a 6% hemoglobin solution was converted to the desoxy form by evacuation to 20 mm Hg followed by flushing with nitrogen. 47 mg of pyridoxal phosphate was added with stirring, which then was continued for 15 minutes. Then 56 mg of sodium borohydride was added and stirring continued for another 20 minutes at room temperature. After further evacuation, 0.8 ml of 10% glutaric dialdehyde was added and stirring continued for another 45 minutes under nitrogen. To separate the uncrosslinked hemoglobin, 90 ml of a 4M ammonium sulfate solution was added over 7 minutes followed by stirring for 10 minutes. The precipitate which formed was centrifuged off and the supernatant matter was discarded. The precipitate was dissolved in 20 ml of water. This was followed by dialysis for 3 hours with a Visking type 10/32 dialyzing hose against a 50 fold volume of an 0.5% common salt solution, the outer solution being replaced three times. For complete removal of the ammonium sulfate, the dialyzed hemoglobin solution was passed over a mixed-bed exchanger formed by a strongly acidic cation exchanger, for example, Dowex WX 8 cation exchanger in the $Na^+$ form, and Dowex 21 K anion exchanger in the $Cl^-$ form, respectively. (Manufacturer: Dow Chemical Company, Midland, Mich.)

After adjustment of the pH value to 7.5 with 1N-NaOH and adjustment to an isotonic electrolyte and glucose concentration, respectively with addition of 2 g of glucose and 0.21 g of sodium bicarbonate, the preparation was sterile-filtered and stored in a refrigerator at 5° C.

Figure 4:
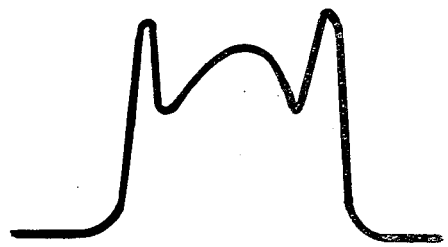
FIGS. 4, 5 and 6 are respectively ir extinction curves of the products of Examples 5, 6 and 7 of this application.

The preparation had a $P_{50}$ value of 16 mm Hg and exhibited the column elution diagram by way of Sepharose 6 B (manufactured by Pharmacia Fine Chemicals AB) shown in FIG. 4.

EXAMPLE 6

Figure 5:
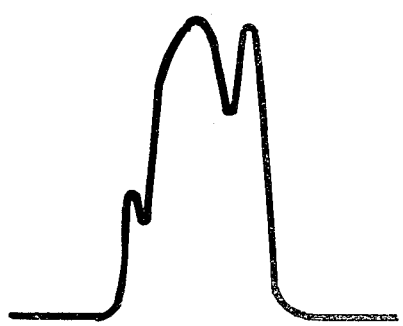

The procedure employed in Example 5 was followed, except that three times as much mix was used before the glutaric dialdehyde was added. After stirring, the preparation was repumped at an inlet pressure of 500 mm Hg through an H1 P 100 hollow-fiber ultrafiltration cartridge prefilled with an 0.9% NaCl solution. The volume separated by pressure through ultrafiltration was continuously replaced with sterile water. The repumping time was about 5 hours. During that time, complete desalting took place simultaneously. The preparation was adjusted as in Example 5, had a $P_{50}$ value of 19 mm Hg and exhibited the gel chromatogram shown in FIG. 5.

EXAMPLE 7

Figure 6:
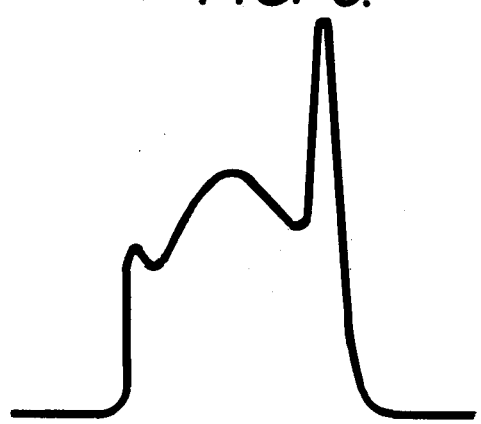

The procedure employed in Example 5 was followed, except that 71 mg of pyridoxal phosphate was added. The end product so obtained was found to have a $P_{50}$ value of 18 mm Hg and gave the gel chromatogram shown in FIG. 6.

It will be appreciated that the instant specification and examples are set forth by way of illustration and not limitation, and that various modifications and changes may be made without departing from the spirit and scope of the present invention.

What is claimed is:

1. A method of manufacturing a hemoglobin preparation, comprising washing human erythrocytes at least four times with a weakly alkaline solution, hemolyzing the erythrocytes in a solvent consisting essentially of water, treating the hemolyzate material with a cation exchange resin in the H+ form until the pH value has dropped to about 5 to 5.5, separating the material from resin and any precipitated stroma, diluting the material with water to a hemoglobin concentration of about 5 to 9%, adjusting the pH to about 7 to 9, displacing any oxygen therein, and adding about 0.25 to 1.25 g of pyridoxal-5-phosphate per liter of hemoglobin solution of 5 to 9% concentration.

2. A method according to claim 1, wherein prior to hemolysis the erythrocytes are first treated with about 4 to 12 g of beta-propiolactone per liter of erythrocytes.

3. A method according to claim 1, wherein glucose monohydrate is added in about 22 g per liter of solution prior to addition of the pyridoxal-5-phosphate.

4. A method according to claim 1, wherein the pH of the solution following addition of the pyridoxal-5-phosphate is adjusted to about 7.6.

5. A method according to claim 2, wherein glucose monohydrate is added in about 22 g per liter of solution prior to addition of the pyridoxal-5-phosphate, and the pH of the solution following addition of the pyridoxal-5-phosphate is adjusted to about 7.6.

6. A method according to claim 1, including the further steps of treating the solution with a borohydride and then with a dialdehyde thereby to cross-link the hemoglobin molecules in said erythrocytes, and separating uncross-linked hemoglobin from the residual solution of the desired cross-linked hemoglobin which latter then has an effective retention time of about 4 to 9 hours following intravenous administration.

7. A method according to claim 6, wherein the borohydride is sodium borohydride and it is employed in about 5 to 10 times the molar amount of the pyridoxal-5-phosphate.

8. A method according to claim 6, wherein the dialdehyde is of the formula $O=CH-(CH_2)_{1-6}-CH=O$ and it is employed in about 9 times the molar amount of the hemoglobin.

9. A method according to claim 6, wherein the pH of the residual solution of the cross-linked hemoglobin solution is adjusted to about 7.6.

10. A method according to claim 9, wherein to the solution of pH about 7.6 glucose monohydrate is added in about 22 g per liter.

11. A method according to claim 2, including the further steps of treating the solution with sodium borohydride in about 5 to 10 times the molar amount of the pyridoxal-5-phosphate and then with a dialdehyde of the formula $O=CH-(CH_2)_{1-6}-CH=O$ in about 9 times the molar amount of the hemoglobin in said erythrocytes thereby to cross-link the hemoglobin molecules, separating uncross-linked hemoglobin from the residual solution of the desired cross-linked hemoglobin, adjusting the pH of the residual solution to about 7.6 and adding about 22 g per liter of glucose monohydrate, whereby the solution has an effective retention time of about 4 to 9 hours following intravenous administration.

12. The product produced by the process of claim 1.

13. The product produced by the process of claim 6.

* * * * *

UNITED STATES PATENT AND TRADEMARK OFFICE
CERTIFICATE OF CORRECTION

PATENT NO. : 4,136,093
DATED : January 23, 1979
INVENTOR(S) Klaus Bonhard et al.

It is certified that error appears in the above-identified patent and that said Letters Patent are hereby corrected as shown below:

First page of the printed patent - item (75) -
Correct spelling of last name of third inventor as follows:

Cancel "Schleubner" and substitute -- Schleussner --

Signed and Sealed this

Sixth Day of November 1979

[SEAL]

Attest:

RUTH C. MASON
*Attesting Officer*

LUTRELLE F. PARKER
*Acting Commissioner of Patents and Trademarks*